(12) United States Patent
Chen et al.

(10) Patent No.: US 8,021,679 B2
(45) Date of Patent: Sep. 20, 2011

(54) NITRIC OXIDE-RELEASING BIODEGRADABLE POLYMERS USEFUL AS MEDICAL DEVICES AND COATINGS THEREFORE

(75) Inventors: Mingfei Chen, Santa Rosa, CA (US); Kishore Udipi, Santa Rosa, CA (US); Peiwen Cheng, Santa Rosa, CA (US)

(73) Assignee: Medtronic Vascular, Inc, Santa Rosa, CA (US)

( * ) Notice: Subject to any disclaimer, the term of this patent is extended or adjusted under 35 U.S.C. 154(b) by 647 days.

(21) Appl. No.: 12/064,112

(22) PCT Filed: Aug. 9, 2006

(86) PCT No.: PCT/US2006/031290
§ 371 (c)(1),
(2), (4) Date: Feb. 19, 2008

(87) PCT Pub. No.: WO2007/024501
PCT Pub. Date: Mar. 1, 2007

(65) Prior Publication Data
US 2008/0220048 A1     Sep. 11, 2008

Related U.S. Application Data

(60) Provisional application No. 60/711,900, filed on Aug. 25, 2005.

(51) Int. Cl.
*A61F 2/00* (2006.01)
*A61F 2/06* (2006.01)

(52) U.S. Cl. ................. 424/426; 623/1.38; 623/1.42

(58) Field of Classification Search .................. None
See application file for complete search history.

(56) References Cited

U.S. PATENT DOCUMENTS

| | | | |
|---|---|---|---|
| 4,954,526 A | 9/1990 | Keefer | |
| 5,039,705 A | 8/1991 | Keefer et al. | |
| 5,155,137 A | 10/1992 | Keefer et al. | |
| 5,212,204 A | 5/1993 | Keefer et al. | |
| 5,250,550 A | 10/1993 | Keefer et al. | |
| 5,268,465 A | 12/1993 | Bredt et al. | |
| 5,362,718 A | 11/1994 | Skotnicki et al. | |
| 5,366,997 A | 11/1994 | Keefer et al. | |
| 5,380,758 A | 1/1995 | Stamler et al. | |
| 5,405,919 A | 4/1995 | Keefer et al. | |
| 5,428,070 A | 6/1995 | Cooke et al. | |
| 5,468,630 A | 11/1995 | Billiar et al. | |
| 5,525,357 A | 6/1996 | Keefer et al. | |
| 5,574,068 A | 11/1996 | Stamler et al. | |
| 5,583,101 A | 12/1996 | Stamler et al. | |
| 5,650,447 A | 7/1997 | Keefer et al. | |
| 5,658,565 A | 8/1997 | Billiar et al. | |
| 5,665,077 A | 9/1997 | Rosen et al. | |
| 5,718,892 A | 2/1998 | Keefer et al. | |
| 5,891,459 A | 4/1999 | Cooke et al. | |
| 5,900,246 A | 5/1999 | Lambert | |
| 5,945,452 A | 8/1999 | Cooke et al. | |
| 6,015,815 A | 1/2000 | Mollison | |
| 6,110,453 A | 8/2000 | Keefer et al. | |
| 6,153,588 A | 11/2000 | Chrzan et al. | |
| 6,224,626 B1 * | 5/2001 | Steinke | 623/1.16 |
| 6,290,981 B1 | 9/2001 | Keefer et al. | |
| 6,306,422 B1 * | 10/2001 | Batich et al. | 424/423 |
| 6,329,386 B1 | 12/2001 | Mollison | |
| 6,403,759 B2 | 6/2002 | Stamler et al. | |
| 6,491,903 B1 * | 12/2002 | Forster et al. | 424/78.01 |
| 6,610,660 B1 | 8/2003 | Saavedra et al. | |
| 6,673,891 B2 | 1/2004 | Stamler et al. | |
| 6,706,274 B2 | 3/2004 | Herrmann et al. | |
| 6,737,447 B1 | 5/2004 | Smith et al. | |
| 6,759,430 B2 | 7/2004 | Anggard et al. | |
| 6,841,166 B1 | 1/2005 | Zhang et al. | |
| 6,875,840 B2 | 4/2005 | Stamler et al. | |
| 6,911,478 B2 | 6/2005 | Hrabie et al. | |
| 6,949,530 B2 | 9/2005 | Hrabie et al. | |
| 6,951,902 B2 | 10/2005 | McDonald et al. | |
| 7,070,798 B1 | 7/2006 | Michal et al. | |
| 7,087,709 B2 | 8/2006 | Stamler et al. | |
| 7,105,502 B2 | 9/2006 | Arnold et al. | |
| 7,378,105 B2 | 5/2008 | Burke et al. | |
| 2002/0094985 A1 | 7/2002 | Herrmann et al. | |
| 2003/0181973 A1 * | 9/2003 | Sahota | 623/1.15 |
| 2004/0037836 A1 | 2/2004 | Stamler et al. | |
| 2004/0171589 A1 | 9/2004 | Herrmann et al. | |
| 2004/0180131 A1 | 9/2004 | Cheng | |
| 2004/0236415 A1 * | 11/2004 | Thomas | 623/1.42 |
| 2005/0058712 A1 * | 3/2005 | Serpelloni et al. | 424/486 |

(Continued)

FOREIGN PATENT DOCUMENTS

| | | |
|---|---|---|
| EP | 0945148 | 9/1999 |
| EP | 0992252 | 4/2000 |
| EP | 1300424 | 4/2003 |
| WO | WO95/24908 | 9/1995 |
| WO | WO96/15797 | 5/1996 |
| WO | WO99/01427 | 1/1999 |
| WO | WO01/10344 | 2/2001 |
| WO | WO2005/039664 | 5/2005 |
| WO | WO2005/081752 | 9/2005 |
| WO | WO2006/037105 | 4/2006 |
| WO | WO2007/024501 | 3/2007 |
| WO | WO2007/053292 | 5/2007 |
| WO | WO2007/053578 | 5/2007 |

OTHER PUBLICATIONS

Ongini et al. Proceedings of the National Academy of Science 2004 101:8497-8502.*
Evans et al. Journal of Organic Chemistry 1995 60:6662-6663.*
Smith et al. Journal of Medicinal Chemistry 1996 39:1148-1156.*
Buellesfeld et al. Herz 2004 29:167-170.*
Trollsas et al. Macromolecules (2000 33:4619-4627.*
Wolfe et al., "Cyclic Hydroxamates, Especially MNultiply Substituted [1,20Oxazinan-3-Ones," Can. J. Chem. 81: pp. 937-960 (2003).
U.S. Appl. No. 12/340,089, filed Dec. 19, 2008.
U.S. Appl. No. 12/422,425, filed Apr. 13, 2009.

(Continued)

*Primary Examiner* — Juliet Switzer
*Assistant Examiner* — Caralynne Helm

(57) ABSTRACT

Nitric Oxide (NO)-releasing polymers useful as implantable medical devices and coatings therefore are provided. Specifically the implantable medical devices and/or coatings comprise NO-releasing biodegradable polymers derived from [1,4] oxazepan-7-one and its derivatives. The medical devices and coatings of the present invention can also be used for in situ controlled release delivery of additional bioactive agents and are useful for treating or preventing medical conditions such as restenosis, aneurysms and vulnerable plaque.

14 Claims, 6 Drawing Sheets

U.S. PATENT DOCUMENTS

| | | |
|---|---|---|
| 2005/0171596 A1 | 8/2005 | Furst et al. |
| 2005/0203069 A1 | 9/2005 | Arnold et al. |
| 2005/0265958 A1 | 12/2005 | West et al. |
| 2005/0281866 A1 | 12/2005 | Jarrett et al. |
| 2006/0008529 A1 | 1/2006 | Meyerhoff et al. |
| 2006/0099235 A1 | 5/2006 | Blakstvedt et al. |
| 2006/0121089 A1 | 6/2006 | Michal et al. |
| 2006/0195142 A1 | 8/2006 | Shalaby |
| 2006/0251824 A1 | 11/2006 | Boulais et al. |
| 2007/0014828 A1 | 1/2007 | Fitzhugh et al. |
| 2007/0053952 A1 | 3/2007 | Chen et al. |
| 2007/0185561 A1 | 8/2007 | Schmitz et al. |
| 2007/0264225 A1 | 11/2007 | Cheng et al. |
| 2008/0220040 A1 | 9/2008 | Cheng et al. |
| 2009/0028966 A1 | 1/2009 | Chen et al. |
| 2009/0222088 A1 | 9/2009 | Chen et al. |
| 2009/0232863 A1 | 9/2009 | Cheng et al. |
| 2009/0232868 A1 | 9/2009 | Chen et al. |

OTHER PUBLICATIONS

Washington State Univ. Lecture, Chemistry 240, Summer 2001, http://chemistry2.csudh.edu/rpendarvis/aminrxn.html.

Reynolds et al., "Nitric Oxide Releasing Polyurethanes with Covalently Linked Diazeniumdiolated Secondary Amines" Biomacromolecules 2006, 7, 987-994.

Tashiro et al., "Removal of Methyl Orange by Systems of Insoluble Poly(Glycidyl Methacrylate)-G-Tetraethylene-Pentamine and -G-Polyethyleneimines", Research Institute for Polymers and Textiles, 205 (1993) 31-45.

Hrabie et al., "New Nitric Oxide-Releasing Zwitterions Derived from Polyamines" J. Org. Chem, 1993, 58, 1472-1476.

Drago et al., "The Reaction of Notrogen(II) Oxide with Diethylamine" Contribution from the W.A. Noyes Laboratory, University of Illinois, Jun. 24, 1959.

Parzuchowski et al., "Synthesis of Potentially More Blood Compatible Nitric Oxide Releasing Acrylic Copolymers" Polymer Preprints, 2001, 42(1), pp. 448-449.

Williams et al. "Nitric Oxide-Releasing Nonsteroidal Anti-Inflammatory Drugs (NSAIDs) Alter the Kinetics of Human Colon Cancer Cell Lines More effectively then Traditional NSAIDs: Implications for Colon Cancer Chemoprevention" Cancer Research, 61, 3285-3289, Apr. 15, 2001, pp. 3285-3289.

Frost et al. "Polymers Incorporating Nitric Oxide Releasing/Generating Substances for Improved Biocompatibility of Blood-Contacting Medical Devices" Biomaterials 26 (2005) 1685-1693.

Deng et al., "Polymerization of Lactides and Lactones 11. Ring-Opening Polymerization of x-Acetyl-y-Butyrolactone and Copolymerization with B-Butyrolactone" European Polymer Journal, 36 (2000) 2739-2741.

Lovric et al., "Scope and Limitations of Sodium and Potassium Trimethylsilanolate as Reagents fro Conversion of Esters to Carboxylic Acids" Croatica Chemica Acta, CCACAA 80 (1), 109-115 (2007).

Kireev et al., "Polymerization of Methyl Methacrylate and Vinyl Acetate Initiated by the Manganese Carbonyl-1,2-Epoxy-4,4,4-Trichlorobutance System" Polymer Science, Ser. B, 2006, vol. 48, Nos. 5-6, pp. 138-141.

Liu et al., "Diethylenetriamine-Grafted Poly(Glycidyl Methacrylate) Adsorbent for Effective Copper Ion Adsorption" Journal of Colloid and Interface Science 303 (2006) 99-108.

Oh et al., "Spontaneous Catalytic Generation of Nitric Oxide from S-Nitrosothiols at the Surface of Polymer Films Doped with Lipophilic Copper (II) Complex" J. Am. Chem. Soc. 203, 125, pp. 9552-9553, 2003.

Abizaid, Alexandre MD "Novel Approaches to New DES Therapies: Where are we Going?" ACC 2007, New Orleans.

Pasterkamp et al., "Atherosclerotic Plaque Rupture: an Overview" J Clin Basic Cardiol, 2000; 3: pp. 81-96.

\* cited by examiner

Polyesters

Poly(ortho esters)

Polyanhydrides

Polyphosphazenes

Formula VII

Formula VIII

Formula IX

Formula X

NITRIC OXIDE-RELEASING BIODEGRADABLE POLYMERS USEFUL AS MEDICAL DEVICES AND COATINGS THEREFORE

FIELD OF THE INVENTION

The present invention relates to medical devices having coatings, wherein the coatings include biodegradable, biocompatible polymers based on modified [1,4]oxazepan-7-one. More specifically, the present invention relates to medical devices having coatings, which include nitric oxide-releasing, biocompatible organic solvent soluble polymers.

BACKGROUND OF THE INVENTION

Nitric oxide (NO) is a simple diatomic molecule that plays a diverse and complex role in cellular physiology. Less than 25 years ago NO was primarily considered a smog component formed during the combustion of fossil fuels mixed with air. However, as a result of the pioneering work of Ferid Murad et al. it is now known that NO is a powerful signaling compound and cytotoxic/cytostatic agent found in nearly every tissue including endothelial cells, neural cells and macrophages. Mammalian cells synthesize NO using a two step enzymatic process that oxidizes L-arginine to N-ω-hydroxy-L-arginine, which is then converted into L-citrulline and an uncharged NO free radical. Three different nitric oxide synthase enzymes regulate NO production. Neuronal nitric oxide synthase (NOSl, or nNOS) is formed within neuronal tissue and plays an essential role in neurotransmission; endothelial nitric oxide synthase (NOS3 or eNOS), is secreted by endothelial cells and induces vasodilatation; inducible nitric oxide synthase (NOS2 or iNOS) is principally found in macrophages, hepatocytes and chondrocytes and is associated with immune cytotoxicity.

Neuronal NOS and eNOS are constitutive enzymes that regulate the rapid, short-term release of small amounts of NO. In these minute amounts NO activates guanylate cyclase which elevates cyclic guanosine monophosphate (cGMP) concentrations which in turn increase intracellular $Ca^{+2}$ levels. Increased intracellular $Ca^{+2}$ concentrations result in smooth muscle relaxation which accounts for NO's vasodilating effects. Inducible NOS is responsible for the sustained release of larger amounts of NO and is activated by extracellular factors including endotoxins and cytokines. These higher NO levels play a key role in cellular immunity.

Medical research is rapidly discovering therapeutic applications for NO including the fields of vascular surgery and interventional cardiology. Procedures used to clear blocked arteries such as percutaneous transluminal coronary angioplasty (PTCA) (also known as balloon angioplasty) and atherectomy and/or stent placement can result in vessel wall injury at the site of balloon expansion or stent deployment. In response to this injury a complex multi-factorial process known as restenosis can occur whereby the previously opened vessel lumen narrows and becomes re-occluded. Restenosis is initiated when thrombocytes (platelets) migrating to the injury site release mitogens into the injured endothelium. Thrombocytes begin to aggregate and adhere to the injury site initiating thrombogenesis, or clot formation. As a result, the previously opened lumen begins to narrow as thrombocytes and fibrin collect on the vessel wall. In a more frequently encountered mechanism of restenosis, the mitogens secreted by activated thrombocytes adhering to the vessel wall stimulate overproliferation of vascular smooth muscle cells during the healing process, restricting or occluding the injured vessel lumen. The resulting neointimal hyperplasia is the major cause of a stent restenosis.

Recently, NO has been shown to significantly reduce thrombocyte aggregation and adhesion; this combined with NO's directly cytotoxic/cytostatic properties may significantly reduce vascular smooth muscle cell proliferation and help prevent restenosis. Thrombocyte aggregation occurs within minutes following the initial vascular insult and once the cascade of events leading to restenosis is initiated, irreparable damage can result. Moreover, the risk of thrombogenesis and restenosis persists until the endothelium lining the vessel lumen has been repaired. Therefore, it is essential that NO, or any anti-restenotic agent, reach the injury site immediately.

One approach for providing a therapeutic level of NO at an injury site is to increase systemic NO levels prophylactically. This can be accomplished by stimulating endogenous NO production or using exogenous NO sources. Methods to regulate endogenous NO release have primarily focused on activation of synthetic pathways using excess amounts of NO precursors like L-arginine, or increasing expression of nitric oxide synthase (NOS) using gene therapy. U.S. Pat. Nos. 5,945,452, 5,891,459 and 5,428,070 describe sustained NO elevation using orally administrated L-arginine and/or L-lysine. However, these methods have not been proven effective in preventing restenosis. Regulating endogenously expressed NO using gene therapy techniques remains highly experimental and has not yet proven safe and effective. U.S. Pat. Nos. 5,268,465, 5,468,630 and 5,658,565, describe various gene therapy approaches.

Exogenous NO sources such as pure NO gas are highly toxic, short-lived and relatively insoluble in physiological fluids. Consequently, systemic exogenous NO delivery is generally accomplished using organic nitrate prodrugs such as nitroglycerin tablets, intravenous suspensions, sprays and transdermal patches. The human body rapidly converts nitroglycerin into NO; however, enzyme levels and co-factors required to activate the prodrug are rapidly depleted, resulting in drug tolerance. Moreover, systemic NO administration can have devastating side effects including hypotension and free radical cell damage. Therefore, using organic nitrate prodrugs to maintain systemic anti-restenotic therapeutic blood levels is not currently possible.

Therefore, considerable attention has been focused on localized, or site specific, NO delivery to ameliorate the disadvantages associated with systemic prophylaxis. Implantable medical devices and/or local gene therapy techniques including medical devices coated with NO-releasing compounds, or vectors that deliver NOS genes to target cells, have been evaluated. Like their systemic counterparts, gene therapy techniques for the localized NO delivery have not been proven safe and effective. There are still significant technical hurdles and safety concerns that must be overcome before site-specific NOS gene delivery will become a reality.

However, significant progress has been made in the field of localized exogenous NO application. To be effective at preventing restenosis an inhibitory therapeutic such as NO must be administered for a sustained period at therapeutic levels. Consequently, any NO-releasing medical device used to treat restenosis must be suitable for implantation. An ideal candidate device is the vascular stent. Therefore, a stent that safely provides therapeutically effective amounts of NO to a precise location would represent a significant advance in restenosis treatment and prevention.

Nitric oxide-releasing compounds suitable for in vivo applications have been developed by a number of investigators. As early as 1960 it was demonstrated that nitric oxide gas could be reacted with amines to form NO-releasing anions having the following general formula 1 R—R'N—N(O)NO wherein R and R' are ethyl. Salts of these compounds could spontaneously decompose and release NO in solution. (R. S. Drago et al., J. Am. Chem. Soc. 1960, 82:96-98)

Nitric oxide-releasing compounds with sufficient stability at body temperatures to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 and in J. A. Hrabie et al., J. Org. Chem. 1993, 58:1472-1476, all of which are herein incorporated by reference.

Briefly, Hrabie et al. describes NO-releasing intramolecular salts (zwitterions) having the general formula 2 RN[N(O)NO$^-$ (CH$_2$)$_x$ NH$_2$$^+$R'.

The [N(O)NO]$^-$ (abbreviated hereinafter as NONO) containing compounds thus described release NO via a first-order reaction that is predictable, easily quantified and controllable (See FIG. 2). This is in sharp contrast to other known NO-releasing compounds such as the S-nitrosothiol series as described in U.S. Pat. Nos. 5,380,758, 5,574,068 and 5,583,101. Stable NO-releasing compounds have been coupled to amine containing polymers. U.S. Pat. No. 5,405,919 ("the '919 patent") describes biologically acceptable polymers that may be coupled to NO-releasing groups including polyolefins, such as polystyrene, polypropylene, polyethylene, polytetrafluoroethylene and polyvinylidene, and polyethylenimine, polyesters, polyethers, polyurethanes and the like. Medical devices, such as arterial stents, composed of these polymers represent a potential means for the site-specific delivery of NO.

Applicants have surprisingly discovered medical devices having coatings, wherein the coatings are comprised of biocompatible, biodegradable polymers based on derivatives of [1,4] oxazepan-7-one, which are NO releasing and thereby inhibit platelet aggregation and adhesion.

SUMMARY OF THE INVENTION

The present invention provides biodegradable polymers suitable for use as medical devices and coatings for medical devices. The polymers made in accordance with the teachings of the present invention are biodegradable, biocompatible, and derived from [1,4] oxazepan-7-one having the general formula directed below as Formula I:

Formula 1

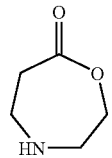

Following ring opening polymerization (ROP), the ring nitrogen provides the polymer backbone with a secondary amine which is a nucleophile center suitable for post-polymerization diazeniumdiolation. Thus the polymers of the present invention are extremely versatile nitric oxide (NO)-releasing and biodegradable.

In one embodiment of the present invention a medical device or its coating, or both, comprise a nitric oxide (NO)-releasing polymer wherein [1,4] oxazepan-7-one is reacted with D,L-lactide and L-lactide in the presence of a polyol such as, but not limited to poly(ethylene glycol) (PEG) and then subjected to a ring opening polymerization (ROP) using a suitable catalyst such as, but not limited to, Tin(II) 2-ethylhexanoate followed by diazeniumdiolation to form a polymer having the general structure according to Formula VIII:

Formula VIII

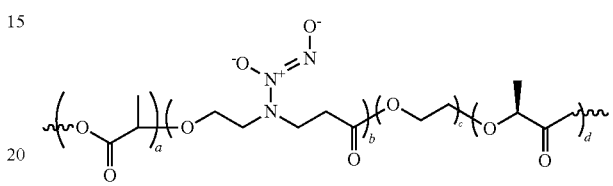

wherein a, b, c, and d each represent repeating units and wherein the ratio of a:b:c:d is a=40-45, b=10-12, c=0.1-0.5 and d=40-45.

In another embodiment of the present invention a medical device or its coating, or both, comprise a (NO)-releasing polymer wherein [1,4] oxazepan-7-one is reacted with D,L-lactide and L-lactide in the presence of a polyol such as, but not limited to, poly(ethylene glycol) (PEG) and then subjected to ROP using a suitable catalyst such as, but not limited to, Tin(II) 2-ethylhexanoate followed by diazeniumdiolation to form a polymer having the general structure according to Formula IX:

Formula IX

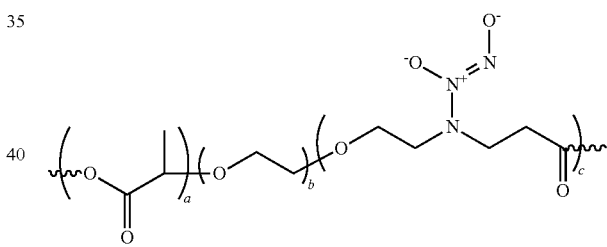

wherein a, b, and c each represent repeating units wherein the ratio of a:b:c is a=90-99, b=0.1-1 and c=0.5-5.

In yet another embodiment of the present invention a medical device or its coating, or both, comprise a NO-releasing polymer wherein [1,4] oxazepan-7-one is reacted with D,L-lactide and ε-caprolactone in the presence of a polyol such as, but not limited to, octanediol and then subjected to ROP using a suitable catalyst such as, but not limited to, Tin(II) 2-ethylhexanoate followed by diazeniumdiolation to form a polymer having the general structure according to Formula X:

Formula X

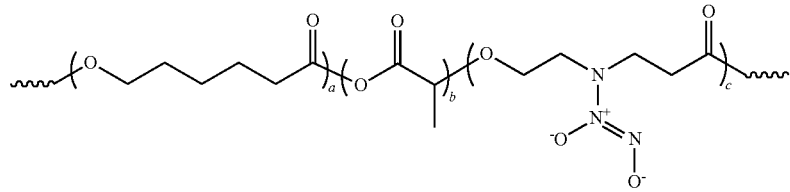

wherein a, b, and c each represent repeating units wherein the ratio of a:b:c is a=1-5, b=90-99 and c=0.1-1.0.

In another embodiment of the present invention a medical device or its coating, or both, comprise a NO-releasing polymer wherein [1,4] oxazepan-7-one is subjected to ROP using a suitable catalyst such as, but not limited to, Tin(II) 2-ethylhexanoate followed by diazeniumdiolation to form a polymer having the monomer repeating unit for Formula VII:

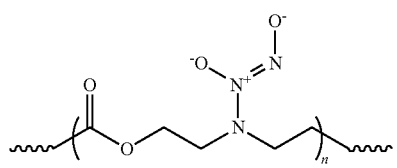

Formula VII

Wherein "n" is any integer from 1 to $10^4$. Moreover, it is also envisioned by the present inventors that [1,4] oxazepan-7-one can be co-polymerized with other compounds as disclosed supra such as, but not limited to, lactide, glycolide, δ-caprolactone, dioxanone, trimethyl carbonate, amino acids, peptides, and other to make biodegradable polymers in accordance with the teachings of the present invention.

The present invention also includes implantable medical devices and coatings for medical devices made from one or more of the NO-releasing polymers of the present invention. Moreover, the NO-releasing medical devices and coating made in accordance with the teachings of the present invention include embodiments wherein one or more additional bioactive agent is eluted from the NO-releasing polymer in a predetermined fashion. Exemplary embodiments of additional bioactive agents include, but are not limited to, drug-eluting vascular stents and coatings therefore wherein antiproliferative bioactive agents are released in situ such that restenosis is treated, prevented or inhibited. Suitable bioactive agents include, but are not limited to, FKBP 12 binding compounds such as zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

DEFINITION OF TERMS

Figure 1:
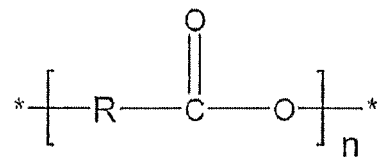
FIG. 1 depicts the chemical structures of the most common biodegradable polymers.
Figure 1:
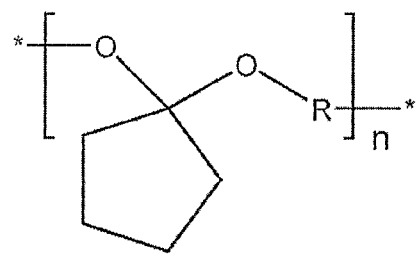
Figure 1:
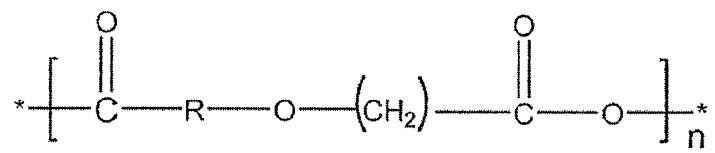
Figure 1:
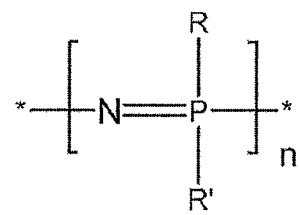

Prior to setting forth the invention, it may be helpful to provide an understanding of the certain terms that will be used hereinafter.

Bioactive agent: As used herein "bioactive agent" shall included anti-proliferative compounds, cytostatic compounds, toxic compounds, anti-inflammatory compounds, analgesics, antibiotics, protease inhibitors, statins, nucleic acids, polypeptides, and delivery vectors including recombinant micro-organisms, liposomes, the like (see Drugs below). The term bioactive agent also encompasses more than one bioactive agent.

Biocompatible: As used herein "biocompatible" shall mean any material that does not cause injury or death to an animal or induce an adverse reaction in an animal when placed in intimate contact with the animal's tissues. Adverse reactions include inflammation, infection, fibrotic tissue formation, cell death, or thrombosis.

Controlled-release: As used herein "controlled-release" refers to the release of a bioactive compound from a medical device surface at a predetermined rate. Controlled-release implies that the bioactive compound does not come off the medical device surface sporadically in an unpredictable fashion and does not "burst" off of the device upon contact with a biological environment (also referred to herein a first-order kinetics) unless specifically intended to do so. However, the term "controlled-release" as used herein does not preclude a "burst phenomenon" associated with deployment. In some embodiments of the present invention an initial burst of drug may be desirable followed by a more gradual release thereafter. The release rate may be steady state (commonly referred to as "timed-release" or zero-order kinetics), that is the drug is released in even amounts over a predetermined time (with or without an initial burst phase) or may be a gradient release. A gradient release implies that the concentration of drug released from the device surface changes over time.

Delayed-Release: As used herein "delayed-release" refers to the release of bioactive agent(s) after a period of time or after an event or series of events.

Drug(s): As used herein "drug" shall include any bioactive agent having a therapeutic effect in an animal. Exemplary, non-limiting examples include anti-proliferatives including, but not limited to, macrolide antibiotics including FKBP 12 binding compounds such as zotarolimus, estrogens, chaperone inhibitors, protease inhibitors, protein-tyrosine kinase inhibitors, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

DETAILED DESCRIPTION OF THE INVENTION

One embodiment of the present invention relates to medical devices and medical device coatings comprising polymers, wherein the polymers and co-polymers are based on [1,4] oxazepan-7-one and derivatives thereof. More specifically, the present invention relates to medical devices and medical device coatings having which include nitric oxide (NO) releasing, biocompatible, biodegradable polymers and co-polymers. Another embodiment of the present invention relates to the method of making medical device and medical device coatings, wherein the medical devices and/or coatings include nitric oxide (NO)-releasing, biocompatible, biodegradable polymers based on derivatives of [1,4] oxazepan-7-one.

The most frequently encountered biodegradable polymers are polyesters, polyorthoesters, polyanhydrides and polyphosphates (see FIG. 1). The present invention provides additional biodegradable, biodegradable polymers having secondary amines in the polymer backbone that can be diazeniumdiolated and are thus useful as NO-releasing coatings and medical devices.

To date, conventional biodegradable polymers such as poly(lactide), poly(caprolactone), poly(glycolide) and their copolymers have been used in the manufacture and use of medical devices and medical device coatings, including, but not limited to, those used on and/or in drug delivery devices and suture materials. However, these polymers are generally hydrophobic in nature and do not possess polymer backbones having free secondary amines. The incorporation of secondary amines into these medical devices and coatings results devices and coatings that are can be diazeniumdiolated and thus NO-releasing.

It is understood that the when the NO-releasing polymers and co-polymers of the present invention are used as coatings they may be comprised of preferably at least about 30%, by weight, more preferably at least about 50%, by weight, and most preferably at least about 80%, by weight, of NO-releasing, biocompatible, biodegradable polymers based on derivatives of [1,4] oxazepan-7-one (see Formula I). Of course, the biodegradable polymer of the present invention may be incorporated either individually or in combination with of any conventional polymer in a medical device and/or a medical device coating.

The present invention provides biodegradable polymers suitable for use as medical devices and coatings for medical devices. The polymers made in accordance with the teachings of the present invention are biodegradable, biocompatible, and derived from [1,4] oxazepan-7-one having the general formula directed below as Formula I:

Formula 1

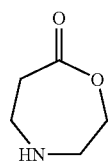

Following ring opening polymerization (ROP), the ring nitrogen provides the polymer backbone with a secondary amine which is a nucleophile center suitable for post-polymerization diazeniumdiolation. Thus the polymers of the present invention are extremely versatile nitric oxide (NO)-releasing and biodegradable.

In one embodiment of the present invention, [1,4] oxazepan-7-one can be reacted with D,L-lactide and L-lactide in the presence of a polyol such as, but not limited to, poly(ethylene glycol) (PEG) and then subjected to a ring opening polymerization (ROP) using a suitable catalyst such as, but not limited to, Tin(II) 2-ethylhexanoate to form a polymer having the general structure according to Formula II:

Formula II

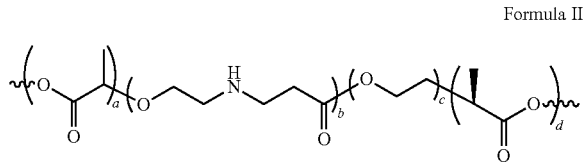

wherein a:b:c:d are repeating units and wherein a=0-20,000, b=1-20,000, c=1-2000 and d=0-20,000. In one embodiment the repeating units a, b, c, and d are present in the polymer in a ratio of a:b:c:d: a=40-45, b=10-12, c=0.1-0.5 and d=40-45.

In another embodiment of the present invention, [1,4] oxazepan-7-one can be reacted with D,L-lactide in the presence of a polyol such as, but not limited to, poly(ethylene glycol) (PEG) and then subjected to ROP using a suitable catalyst such as, but not limited to, Tin(II) 2-ethylhexanoate to form a polymer having the general structure according to Formula III:

Formula III

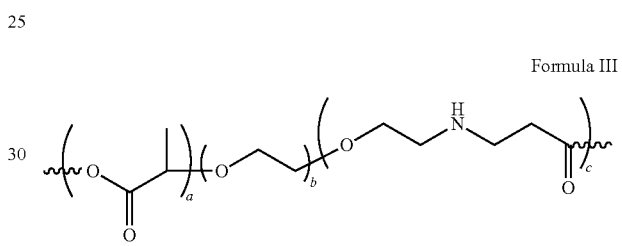

wherein a:b:c are repeating units and wherein a=0-20,000, b=1-2000 and c=1-20,000. In one embodiment the repeating units a, b, and c, are present in the polymer in a ratio of a:b:c wherein a=90-99, b=0.1-1 and c=0.5-2.0.

In yet another embodiment of the present invention, [1,4] oxazepan-7-one can be reacted with D,L-lactide and ε-caprolactone in the presence of a polyol such as, but not limited to, octanediol and then subjected to ROP using a suitable catalyst such as, but not limited to, Tin(II) 2-ethylhexanoate to form a polymer having the general structure according to Formula IV:

Formula IV

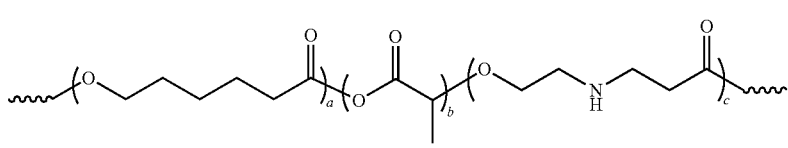

wherein a:b:c are repeating units for each polymer and wherein a=0-20,000, b=1-20,000 and c=1-20,000. In one embodiment the repeating units a, b, and c, are present in the polymer in a ratio of a:b:c wherein a=1-5, b=90-99 and c=0.1-1.0.

In another embodiment of the present invention, [1,4] oxazepan-7-one can be subjected to ROP using a suitable catalyst such as, but not limited to, Tin(II) 2-ethylhexanoate to form a polymer having the monomer repeating unit for Formula V:

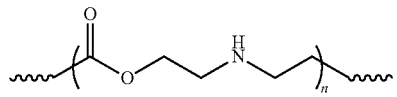

Formula V wherein "n" is any integer from 1 to $10^7$. Moreover, it is also envisioned by the present inventors that [1,4] oxazepan-7-one can be co-polymerized with other compounds as disclosed supra such as, but not limited to, lactide, glycolide, δ-caprolactone, dioxanone, trimethyl carbonate, amino acids, peptides, and other to make amphiphilic biodegradable polymers in accordance with the teachings of the present invention.

The polymers of Formulas II-V made in accordance with the teachings of the present invention are treated using nitric oxide gas under pressure such that the secondary amines in the polymer back bone are provided With a nitric oxide releasing functional group having the structure of Formula VI.

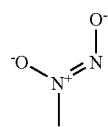

Formula VI

The present invention also includes implantable medical devices and coatings for medical devices made from one or more of the NO-releasing polymers of the present invention. Moreover, the NO-releasing medical devices and coating made in accordance with the teachings of the present invention include embodiments wherein one or more additional bioactive agent is eluted from the NO-releasing polymer in a predetermined fashion. Exemplary embodiments of additional bioactive agents include, but are not limited to, drug-eluting vascular stents and coatings therefore wherein anti-proliferative bioactive agents are released in situ such that restenosis is treated, prevented or inhibited. Suitable bioactive agents include, but are not limited to, FKBP 12 binding compounds such as zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

Thus the present invention provides at least two means for enhancing a medical device's biocompatibility and/or providing for in situ drug delivery to a treatment site. In one embodiment of the present invention the biocompatible, biodegradable, NO-releasing polymers and co-polymers made in accordance with the teachings of the present invention are used to provide coatings for implantable medical devices; the coating may or may not include an additional bioactive agent. In another embodiment of the present invention the entire medical device is made using the biocompatible, biodegradable, NO-releasing polymers and co-polymers made in accordance with the teachings of the present invention.

Biodegradable medical devices made in accordance with the teachings of the present invention include, but are not limited to, vascular stents, stent grafts, urethral stent, biliary stents, catheters, sutures, ocular devices, heart valves, shunts, pacemakers, bone screws and anchors, protective plates and prosthetic devices, both functional and cosmetic. The implantable medical device may be composed of the biodegradable, biocompatible polymers of the present invention, or may be coated with the polymers of the present invention. Moreover, in one embodiment of the present invention, the implantable medical device is made entirely from the biocompatible, biodegradable polymers of the present invention and is additionally coated with at least one polymer made in accordance with the teachings of the present invention.

Although myriad medical conditions can be treated and prevented using medical devices that are composed of, or incorporate, the coatings of the present invention, the present inventors have selected vascular stents and stent grafts as non-limiting enabling examples of the present invention. Thus, stents, stent coatings and method for using stents, coated and non-coated, will now be discussed in detail.

Vascular stents present a particularly unique challenge for the medical device coating scientist. Vascular stents (hereinafter referred to as "stents") must be flexible, expandable, biocompatible and physically stable. Stents are used to relieve the symptoms associated with coronary artery disease caused by occlusion in one or more coronary artery. Occluded coronary arteries result in diminished blood flow to heart muscles causing ischemia induced angina and in severe cases myocardial infarcts and death. Stents are generally deployed using catheters having the stent attached to an inflatable balloon at the catheter's distal end. The catheter is inserted into an artery and guided to the deployment site. In many cases the catheter is inserted into the femoral artery or of the leg or carotid artery and the stent is deployed deep within the coronary vasculature at an occlusion site.

Vulnerable plaque stabilization is another application for coated drug-eluting vascular stents. Vulnerable plaque is composed of a thin fibrous cap covering a liquid-like core composed of an atheromatous gruel. The exact composition of mature atherosclerotic plaques varies considerably and the factors that affect an atherosclerotic plaque's make-up are poorly understood. However, the fibrous cap associated with many atherosclerotic plaques is formed from a connective tissue matrix of smooth muscle cells, types I and III collagen and a single layer of endothelial cells. The atheromatous gruel is composed of blood-borne lipoproteins trapped in the subendothelial extracellular space and the breakdown of tissue macrophages filled with low density lipids (LDL) scavenged from the circulating blood. (G. Pasterkamp and E. Falk. 2000. Atherosclerotic Plaque Rupture: An Overview. J. Clin. Basic Cardiol. 3:81-86). The ratio of fibrous cap material to atheromatous gruel determines plaque stability and type. When atherosclerotic plaque is prone to rupture due to instability it is referred to as "vulnerable" plaque. Upon rupture the atheromatous gruel is released into the blood stream and induces a massive thrombogenic response leading to sudden coronary death. Recently, it has been postulated that vulnerable plaque can be stabilized by stenting the plaque. Moreover, vascular stents having a drug-releasing coating composed of matrix metalloproteinase inhibitor dispersed in, or coated with (or both) a polymer may further stabilize the plaque and eventually lead to complete healing.

Treatment of aneurysms is another application for drug-eluting stents. An aneurysm is a bulging or ballooning of a blood vessel usually caused by atherosclerosis. Aneurysms occur most often in the abdominal portion of the aorta. At least 15,000 Americans die each year from ruptured abdominal aneurysms. Back and abdominal pain, both symptoms of an abdominal aortic aneurysm, often do not appear until the aneurysm is about to rupture, a condition that is usually fatal. Stent grafting has recently emerged as an alternative to the standard invasive surgery. A vascular graft containing a stent (stent graft) is placed within the artery at the site of the aneurysm and acts as a barrier between the blood and the weakened wall of the artery, thereby decreasing the pressure on artery. The less invasive approach of stent-grafting aneurysms decreases the morbidity seen with conventional aneurysm repair. Additionally, patients whose multiple medical comorbidities place them at an excessively high risk for conventional aneurysm repair are candidates for stent-grafting. Stent-grafting has also emerged as a new treatment for a related condition, acute blunt aortic injury, where trauma causes damage to the artery.

Once positioned at the treatment site the stent or graft is deployed. Generally, stents are deployed using balloon catheters. The balloon expands the stent gently compressing it against the arterial lumen clearing the vascular occlusion or stabilizing the aneurysm. The catheter is then removed and the stent remains in place permanently. Most patients return to a normal life following a suitable recovery period and have no reoccurrence of coronary artery disease associated with the stented occlusion. However, in some cases the arterial wall's intima is damaged either by the disease process itself or as the result of stent deployment. This injury initiates a complex biological response culminating is vascular smooth muscle cell hyperproliferation and occlusion, or restenosis at the stent site.

Recently significant efforts have been devoted to preventing restenosis. Several techniques including brachytherapy, excimer laser, and pharmacological techniques have been developed. The least invasive and most promising treatment modality is the pharmacological approach. A preferred pharmacological approach involves the site-specific delivery of cytostatic or cytotoxic drugs directly to the stent deployment area. Site-specific delivery is preferred over systemic delivery for several reasons. First, many cytostatic and cytotoxic drugs are highly toxic and cannot be administered systemically at concentrations needed to prevent restenosis. Moreover, the systemic administration of drugs can have unintended side effects at body locations remote from the treatment site. Additionally, many drugs are either not sufficiently soluble, or too quickly cleared from the blood stream to effectively prevent restenosis. Therefore, administration of anti-restenotic compounds directly to the treatment area is preferred.

Several techniques and corresponding devices have been developed to deploy anti-restenotic compounds including weeping balloon catheters and injection catheters. Weeping balloon catheters are used to slowly apply an anti-restenotic composition under pressure through fine pores in an inflatable segment at or near the catheter's distal end. The inflatable segment can be the same used to deploy the stent or a separate segment. Injection catheters administer the anti-restenotic composition by either emitting a pressurized fluid jet, or by directly piercing the artery wall with one or more needle-like appendage(s) Recently, needle catheters have been developed to inject drugs into an artery's adventitia. However, administration of anti-restenotic compositions using weeping catheters and injection catheters to prevent restenosis remains experimental and largely unsuccessful. Direct anti-restenotic composition administration has several disadvantages. When anti-restenotic compositions are administered directly to the arterial lumen using a weeping catheter, the blood flow quickly flushes the anti-restenotic composition downstream and away from the treatment site. Anti-restenotic compositions injected into the lumen wall or adventitia may rapidly diffuse into the surrounding tissue. Consequently, the anti-restenotic composition may not be present at the treatment site in sufficient concentrations to prevent restenosis. As a result of these and other disadvantages associated with catheter-based local drug delivery, investigators continue to seek improved methods for the localized delivery of anti-restenotic compositions.

Figure 2:
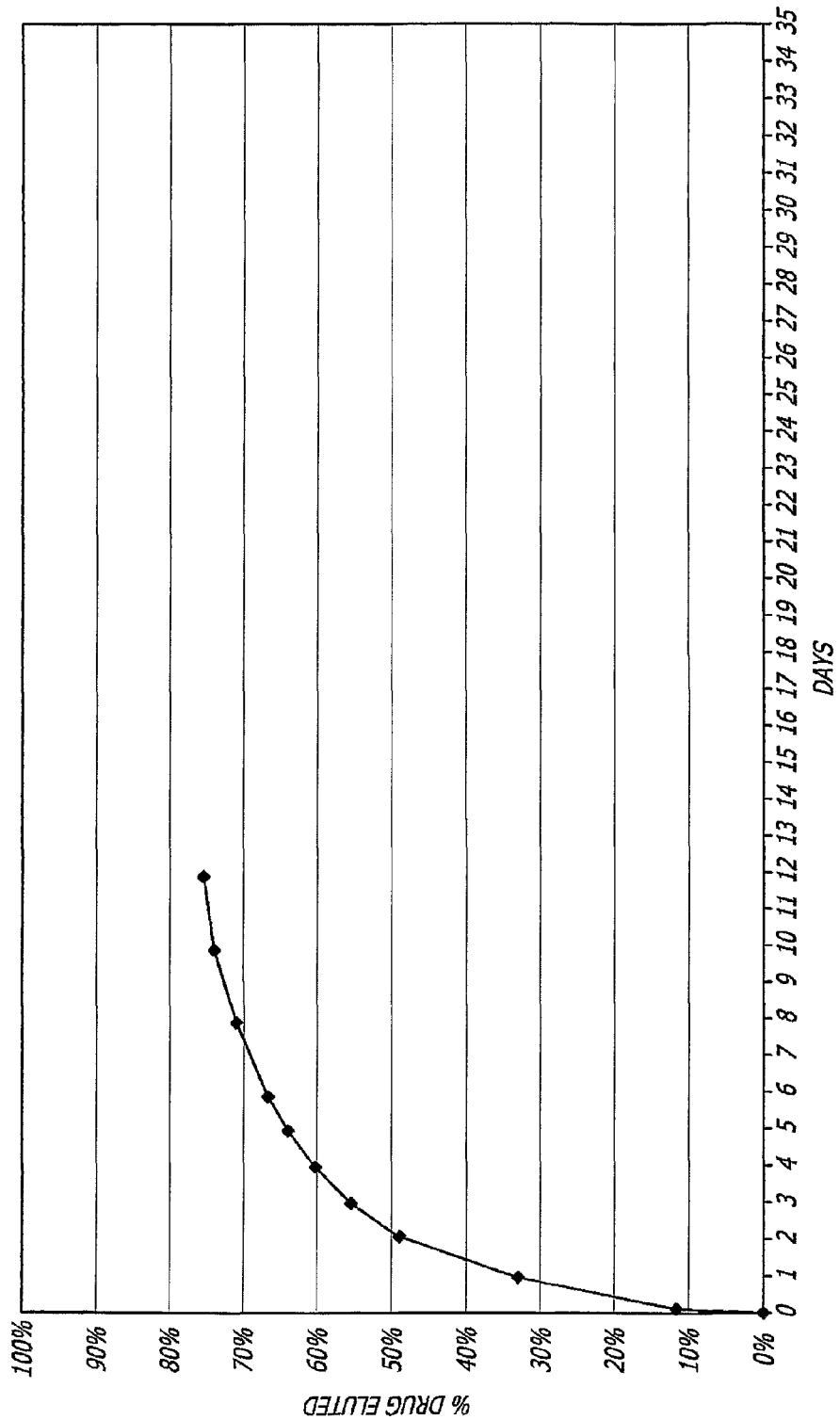
FIG. 2 graphically depicts idealized first-order kinetics associated with drug release from a polymer coating.
Figure 3:
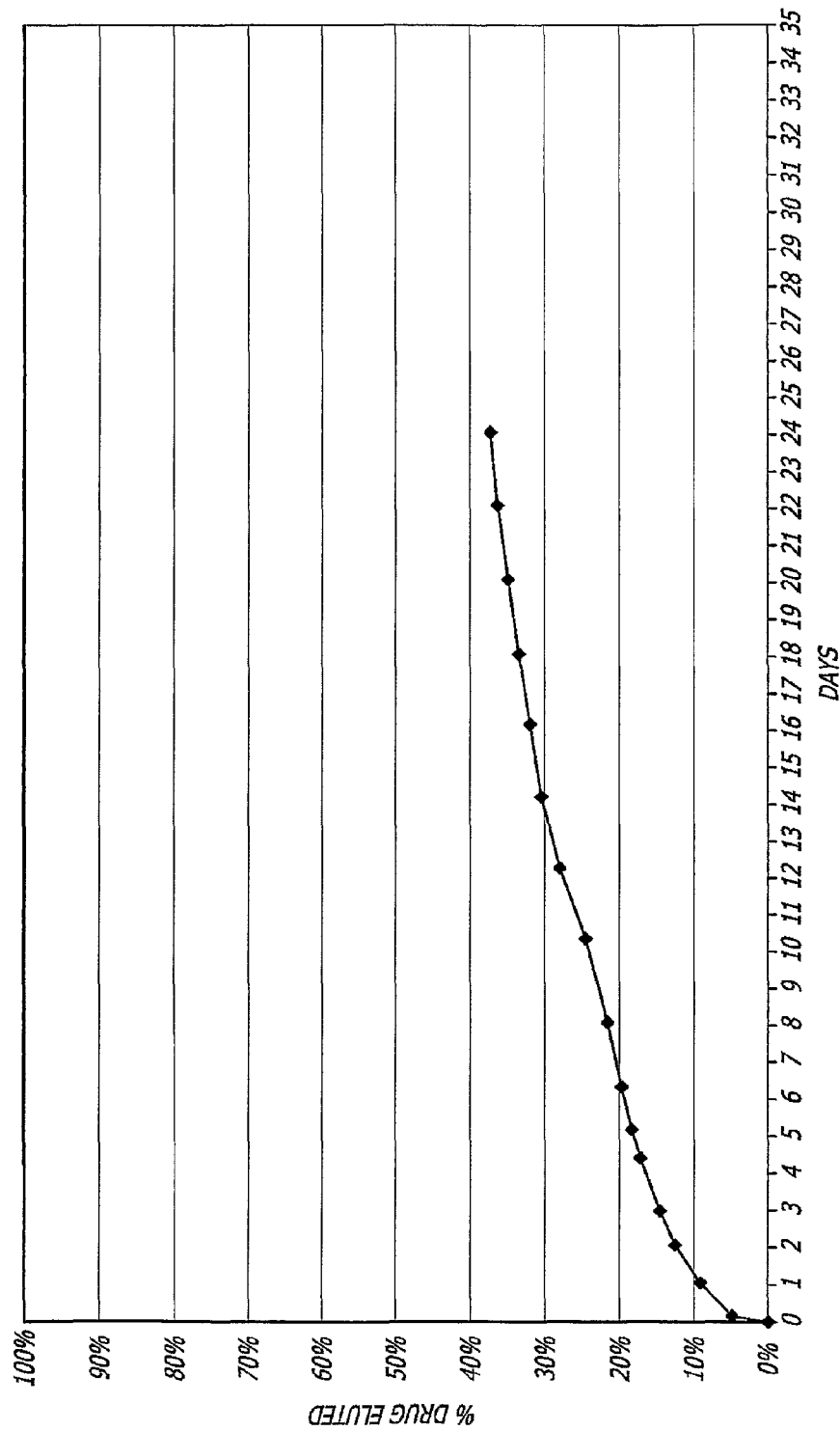
FIG. 3 graphically depicts idealized zero-order kinetics associated with drug release from a polymer coating.

The most successful method for localized anti-restenotic composition delivery developed to date is the drug-eluting stent. Many drug-eluting stent embodiments have been developed and tested. However, significant advances are still necessary in order to provide safe and highly effective drug delivery stents. One of the major challenges associated with stent-based anti-restenotic composition delivery is controlling the drug delivery rate. Generally speaking, drug delivery rates have two primary kinetic profiles. Drugs that reach the blood stream or tissue immediately after administration follow first-order kinetics. First-order drug release kinetics provide an immediate surge in blood or local tissue drug levels (peak levels) followed by a gradual decline (trough levels). In most cases, therapeutic levels are only maintained for a few hours. Drugs released slowly over a sustained time where blood or tissue concentrations remains steady follow zero-order kinetics. Depending on the method of drug delivery and tissue/blood clearance rates, zero-order kinetics result in sustained therapeutic levels for prolonged periods. Drug-release profiles can be modified to meet specific applications. Generally, most controlled release compositions are designed to provide near zero-order kinetics (see FIG. 3). However, there may be applications where an initial burst, or loading dose, of drug is desired (first-order kinetics, see FIG. 2) followed by a more gradual sustained drug release (near zero-order kinetics). Nitric Oxide release from a in situ medical device made in accordance with the teachings of the present invention is generally first order.

As discussed briefly supra, the biocompatible, biodegradable, amphiphilic polymers of the present invention are based on derivatives and co-polymers of N-acetyl-caprolactone having the general structure of Formula I. N-acetyl-caprolactone can be used alone to make the polymer of Formula V or it may be copolymerized with other known monomers to form a mixed biodegradable polymer of the present invention. Other known monomers include, but are not limited to, poly (lactide), poly(caprolactone), poly(glycolide), dioxanone, trimethylene carbonate, glycolide, amino acids, peptides and their derivatives. The following non-limiting Examples provide teachings for making representative biodegradable, biocompatible polymers of the present invention.

EXAMPLES

All of the reagents used in making the biodegradable, biocompatible polymers of the present invention are readily available from commercial sourced such as, but not limited to, Sigma-Aldrich Chemicals, St. Louis, Mo., USA. The common starting material, [1,4] oxazepan-7-one, can be synthesized from 4-piperidone using methods know in the art:

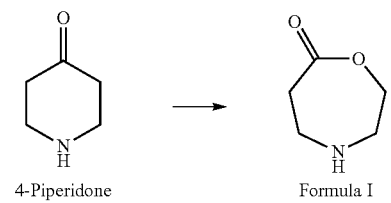

4-Piperidone → Formula I

Example 1

Synthesis of Biodegradable Polymer of Formula II

Formula II

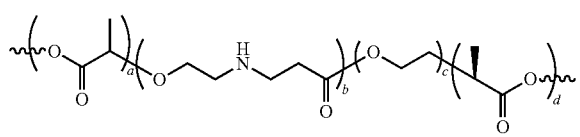

The ratio of a:b:c:d is a=40-45, b=10-12, c=0.1-0.5 and d=40-45.

In one embodiment of the present invention, the polymer of Formula II can be synthesized as follows: 0.5 gram of PEG-3400, 5 gram of D,L-lactide (3,6-dimethyl-1,4-dioxane-2,5-dione), 5 gram of L-lactide ((3s)-cis-3, 6-dimethyl-1, 4-dioxane-2, 5-dione), approximately 1 gram of [1,4] oxazepan-7-one and 0.12 gram of Tin (II) 2-ethyl hexanoate are added into a 100 mL glass serum bottle. A Teflon-coated magnetic stir bar is added into the bottle and the bottle was sealed with Teflon-coated silicon septum with crimper. The reaction bottle is purged with nitrogen for 20 minutes and then placed in a 140° C. silicon oil bath with a stir bar in it for 72 hours. The reactant is dissolved in 20 mL chloroform and poured into about 200 mL of methanol for precipitation. This procedure is repeated three times. The final purified polymer is dissolved in chloroform and poured into a PTFE tray. The tray is placed in a vacuum oven at 50° C. overnight.

General Reaction for Making the Polymer of Formula II

General Reaction for Making the Polymer of Formula II

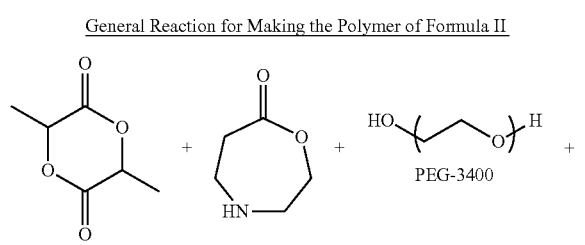

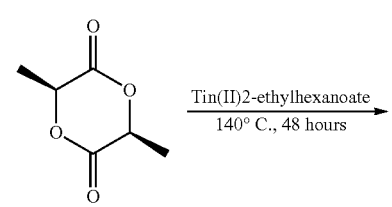

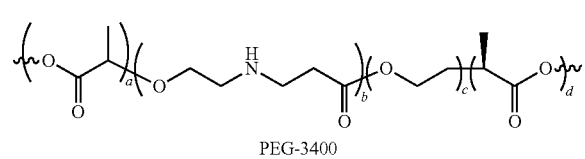

PEG-3400 a:b:c:d = 44:11.8:0.2:44

Example 2

Synthesis of Biodegradable Polymer of Formula III

Formula III

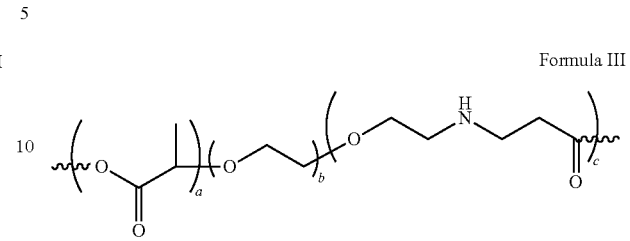

The ratio of a:b:c is a=90-99, b=0.1-1 and c=0.5-2.0.

In one embodiment of the present invention, the polymer of Formula III may be synthesized as follows: 0.5 gram of PEG-3400, 9 gram of D,L-lactide (3,6-dimethyl-1,4-dioxane-2,5-dione), approximately 0.5 gram of [1,4] oxazepan-7-one and 0.10 gram of Tin (II) 2-ethyl hexanoate are added into a 100 mL glass serum bottle. A Teflon-coated magnetic stir bar is added into the bottle and the bottle was sealed with a Teflon-coated silicon septum with crimpier. The reaction bottle is purged with nitrogen for 20 minutes and then placed in a 140° C. silicon oil bath with a stir bar in it for 72 hours. The reactant is dissolved in 20 mL chloroform and poured into about 200 mL of methanol for precipitation. This procedure is repeated three times. The final purified polymer is dissolved in chloroform and poured into a PTFE tray. The tray is placed in a vacuum oven at 50° C. overnight.

General Reaction for Making the Polymer of Formula III

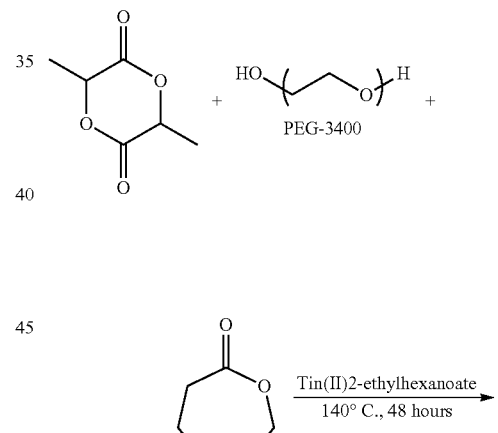

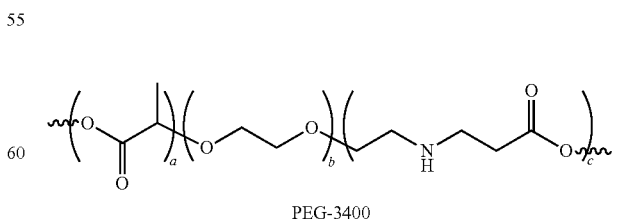

PEG-3400 a:b:c = 99:0.13:0.87

Example 3

Synthesis of Biodegradable Polymer Having the Formula IV

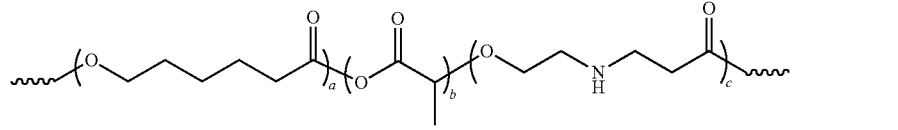

Formula IV

The ratio of a:b:c is a=1-5, b=90-99 and c=0.1 to 1.0.

In one embodiment of the present invention, the polymer of Formula IV may be synthesized as follows: 9 gram of D,L-lactide (3,6-dimethyl-1,4-dioxane-2,5-dione), approximately 0.5 gram of [1,4] oxazepan-7-one, 0.5 gram of ε-caprolactone and 0.10 gram of Tin (II) 2-ethyl hexanoate are add into a 100 mL glass serum bottle. A Teflon-coated magnetic stir bar is added into the bottle and the bottle was sealed with Teflon-coated silicon septum with crimpier. The reaction bottle is purged with nitrogen for 20 minutes and the placed in a 140° C. silicon oil bath with a stir bar in it for 72 hours. The reactant is dissolved in 20 mL chloroform and poured into about 200 mL of methanol for precipitation. This procedure is repeated three times. The final purified polymer is dissolved in chloroform and poured into a PTFE tray. The tray is placed in a vacuum oven at 50° C. overnight.

General Reaction for Making the Polymer of Formula 4

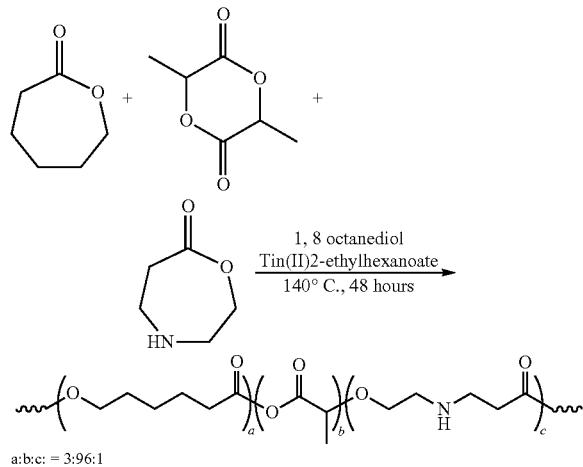

a:b:c: = 3:96:1

Example 4

Diazeniumdiolation of the Polymers Made in Accordance with the Teachings of Examples 1 to 3

Figure 7:
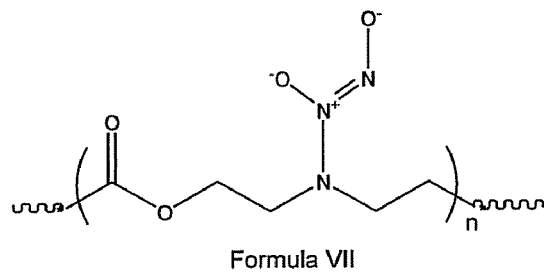
FIG. 7 depicts exemplary NO-releasing polymers made in accordance with the teachings of the present invention (Formulas VII though X).
Figure 7:
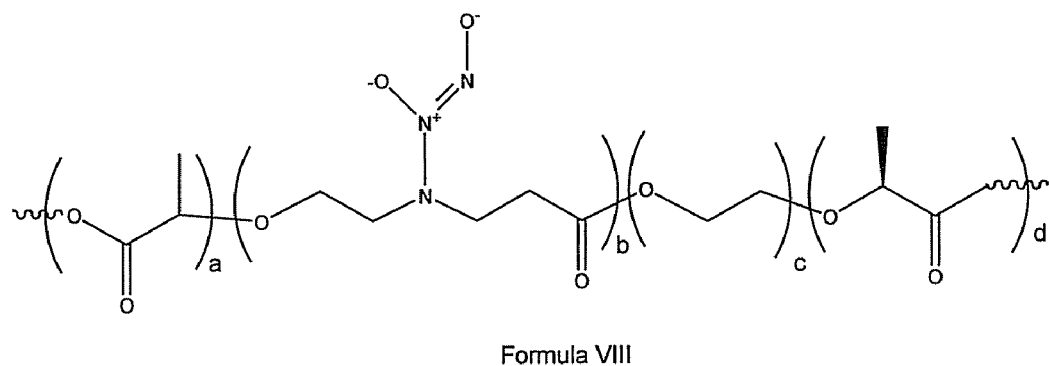
Figure 7:
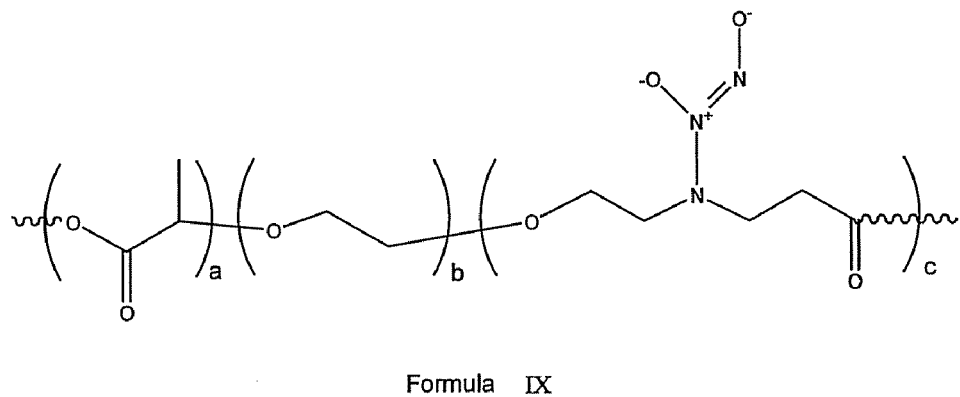
Figure 7:
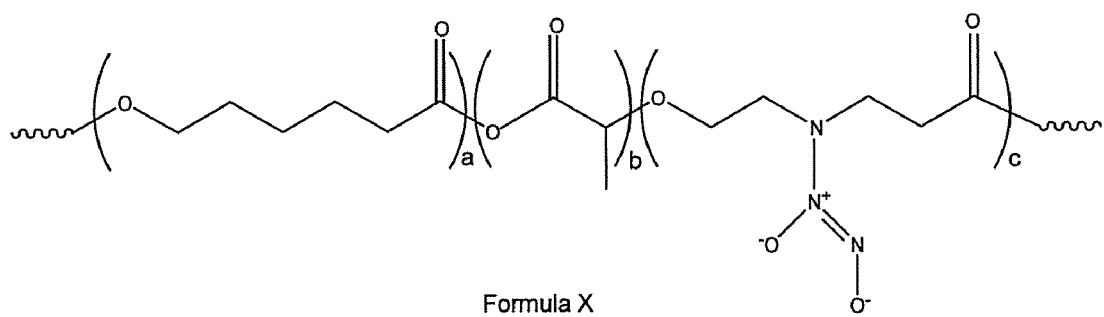

A polymer having at least one monomeric subunit according to Formula V is dissolved in a suitable organic solvent such as chloroform or tetrahydrofuran (THF). At this step, one or more bioactive agents such as, but not limited to, zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids may be included in the polymer solution. Next the solubilized polymer (with or without added bioactive agents) is applied to the surfaces of an implantable medical device using methods known to those skilled in the art such as, but not limited to, rolling, dipping, spraying and painting. Excess polymer is removed under a gentle stream of warm inert gas such as, but not limited to argon or bone-dry nitrogen. The coated medical device is then diazeniumdiolated according to the following reaction to obtain a polymer or copolymer according to Formulas I through IV wherein the secondary amine-containing monomeric subunit has a NO-releasing NONate group according to Formula VII (see FIG. 7).

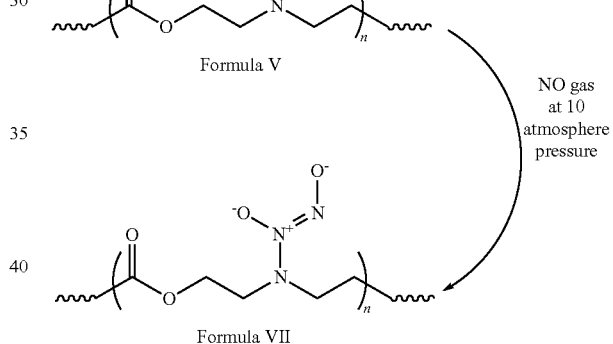

wherein "n" is an integer from 1 to $10^4$. Note that only the monomer derived form a ROP using [1,4] oxazepan-7-one is depicted in Formula VII. Thus when the polymers depicted in Formulas II through IV are diazeniumdiolated in accordance with the teachings of the present invention NO releasing polymers VIII through X result:

Formula VIII

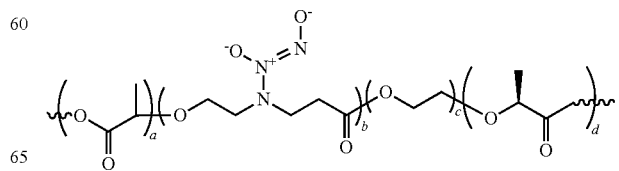

wherein a, b, c, and d each represent repeating units and wherein the ratio of a:b:c:d is: a=40-45, b=10-12, c=0.1-0.5 and d=40-45.

Formula IX

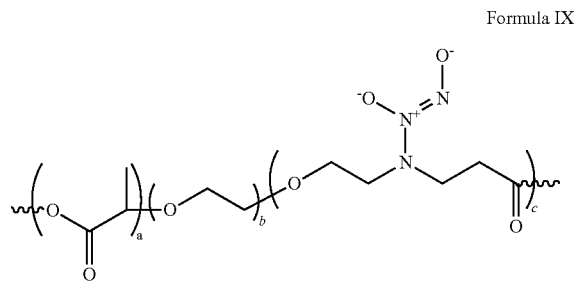

wherein a, b, and c each represent repeating units wherein the ratio of a:b:c is: a=90-99, b=0.1-1 and c=0.5-2.0.

Formula X

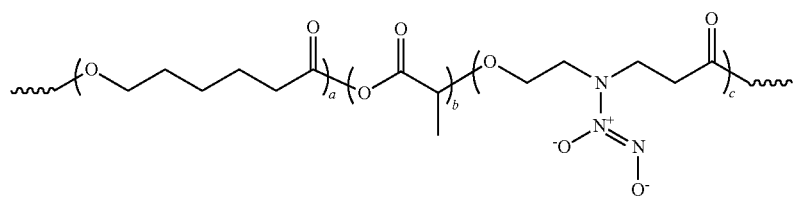

wherein a, b, and c each represent repeating units wherein the ratio of a:b:c is: a=1-5, b=90-99 and c=0.1-1.0.

Moreover, it is also possible to fabricate a medical device, such as a vascular stent from a polymer or copolymer made in accordance with the teachings of the present invention and then diazeniumdiolate the device as describe supra such that the entire device is NO-releasing. Suitable non-limiting examples for fabricating a device using the polymers and copolymers of the present invention are described in detail infra.

A vascular stent coated with, or fabricated from, at least one polymer of Examples 1 through IV is placed in a 13 mm×100 mm glass test tube. Ten milliliters of 3% sodium methylate in methanol or acetonitrile is added to the test tube, which is then placed in a 250 mL stainless steel Parr® hydrogenation vessel. The vessel is degassed by repeated cycles (×10) of pressurization/depressurization with nitrogen gas at 10 atmospheres. Next, the vessel undergoes 2 cycles of pressurization/depressurization with NO at 30 atmospheres. Finally, the vessel is filled with NO at 30 atmospheres and left at room temperature for 24 hrs. After 24 hrs, the vessel is purged of NO and pressurized/depressurized with repeated cycles (×10) of nitrogen gas at 10 atmospheres. The test tube is removed from the vessel and the 3% sodium methylate solution is decanted. The stent is then washed with 10 mL of methanol (×1) and 10 mL of diethyl ether (×3). The stent is then removed from the test tube and dried under a stream of nitrogen gas. This procedure results in a diazeniumdiolated polymer-coated vascular stent.

It is understood that other methods may be used to provided the polymer according to Formula II with NO-releasing functionality, see for example U.S. Pat. No. 5,405,919 (the entire contents of which are hereby incorporated herein by reference) for other examples.

The present invention is directed at optimized drug-releasing medical device coatings and medical devices themselves comprised entirely, or nearly entirely from polymers of the present invention that are suitable for use in hemodynamic environments. The coatings and devices of the present invention may also have at least one bioactive compound or drug dispersed therein in addition to NO.

Example 5

Methods for Making Coatings for Implantable Medical Devices Using the Polymers of Examples 1-3; Co-solvent of Drug/Polymer System (Drug Loading 30%)

Weigh 0.25 g of zotarolimus (formerly known as ABT-578) in a small-neck glass bottle. Add 25 mL of methylene chloride to the same bottle. Mix the solution until a clear solution is achieved. Weigh 0.25 g of degradable polymer made in accordance with the teachings of the present invention into a small weighing pan and transfer it into a same small neck bottle. Add 25 mL of methylene chloride into the bottle. Mix the solution as before until a clear solution is achieved. Using micropipette transfer 3 mL of zotarolimus/methylene chloride solution into a small-neck glass bottle. Using micropipette transfer 7 mL of polymer/methylene chloride solution into the same small-neck glass bottle. Mix the drug/polymer solution on a MAXMIXII mixer. Filter the drug/polymer solution through a 0.45 um PTFE filter into another pre-cleaned small-neck bottle.

The solution is then sprayed on a stent. Place the coated stent in a IIB2 hood overnight and weigh the dried post-coated stent.

Example 6

Methods for Making Coatings for Implantable Medical Devices Using the Polymers of Examples 1-3; Co-solvent of Drug/Polymer System (Drug Loading 25%

Weigh 0.25 g of zotarolimus in a small-neck glass bottle. Add 25 mL of methylene chloride to the same bottle. Mix the solution until a clear solution is achieved. Weigh 0.25 g of degradable polymer made in accordance with the teachings of the present invention into a small weighing pan and transfer it into a same small-neck bottle. Add 25 mL of methylene chloride into the bottle. Mix the solution as before until a clear solution is achieved. Using a micropipette transfer 2.5 mL of zotarolimus/methylene chloride solution into a small-neck glass bottle. Using a micropipette transfer 7.5 mL of polymer/methylene chloride solution into the same small neck-glass bottle. Mix the drug/polymer solution on a MAXMIXII mixer. Filter the drug/polymer solution through a 0.45 um PTFE filter into another pre-cleaned small-neck bottle.

The solution is then sprayed on the stent. Place the coated stent in a IIB2 hood overnight and weigh the dried post-coated stent.

The present invention is directed at optimized drug releasing medical device coatings and medical devices themselves comprised entirely, or nearly entirely from biodegradable polymers of the present invention that are suitable for use in hemodynamic environments. The coatings and devices of the present invention may also have at least one bioactive compound or drug dispersed therein.

In addition to the aforementioned structural and drug-releasing profile considerations, polymers used as stent coatings must also be biocompatible. Biocompatibility encompasses numerous factors that have been briefly defined in the preceding "Definition of Terms" section. The need for a polymer to be biocompatible significantly limits the number of available options for the material scientist. Moreover, these options are further limited when the polymer coating is used on a device that is continuously exposed to hemodynamic forces. For example, stent coatings must remain non-thrombogenic, non-inflammatory and structurally stable for prolonged time periods.

Therefore, there are four specific attributes that the stent coating polymers made in accordance with the teachings of the present invention should possess. The polymer compositions of the present invention should be biocompatible, degrade at a predetermined rate, be elastic/ductile and possess a predetermined drug release profile. Other requirements include processing compatibility such as inert to sterilization methods including, but not limited to, ethylene oxide sterilization. The present invention provides novel polymer compositions made in accordance with the teachings of the present invention.

Release rate is not entirely a function of drug-polymer compatibility. Coating configurations, polymer swellability, and coating thickness also play roles. Moreover, the present invention provides yet another means for controlling drug elution rates. By tuning the biodegradable polymers of the present invention to degrade at a specific rate, drug elution can be precisely controlled and ceases entirely with the complete degradation of the polymer.

When the medical device of the present invention is used in the vasculature, the coating dimensions are generally measured in micrometers (μm). Coatings consistent with the teaching of the present invention may be a thin as 1 μm or a thick as 1000 μm. There are at least two distinct coating configurations within the scope of the present invention. In one embodiment of the present invention the drug-containing coating is applied directly to the device surface or onto a polymer primer. Depending on the solubility rate and profile desired, the drug is either entirely soluble within the polymer matrix, or evenly dispersed throughout. The drug concentration present in the polymer matrix ranges from 0.1% by weight to 80% by weight. In either event, it is most desirable to have as homogenous of a coating composition as possible. This particular configuration is commonly referred to as a drug-polymer matrix.

Finally, returning to coating thickness, while thickness is generally a minor factor in determining overall drug-release rates and profile, it is nevertheless an additional factor that can be used to tune the coatings. Basically, if all other physical and chemical factors remain unchanged, the rate at which a given drug diffuses through a given coating is directly proportional to the coating thickness. That is, increasing the coating thickness increases the elution rate and visa versa.

We now turn to another factor that contributes to the compatibilized, biodegradable controlled-release coatings of the present invention. As mentioned earlier, coating intended for medical devices deployed in a hemodynamic environment must possess excellent adhesive properties. That is, the coating must be stably linked to the medical device surface. Many different materials can be used to fabricate the implantable medical devices including, but not limited to, stainless steel, nitinol, aluminum, chromium, titanium, gold, cobalt, ceramics, and a wide range of synthetic polymeric and natural materials including, but not limited to, collagen, fibrin and plant fibers. All of these materials, and others, may be used with the controlled-release coatings made in accordance with the teachings of the present invention. Furthermore, the biodegradable polymers of the present invention can be used to fabricate an entire medical device such that the bioactive agent is dispersed throughout the polymer and released as the device degrades. This feature of the present invention is particularly useful when the device is implanted into remote regions of the body where subsequent removal, should it be required, is either not possible or involves complex, high risk surgical procedures.

Figure 4:
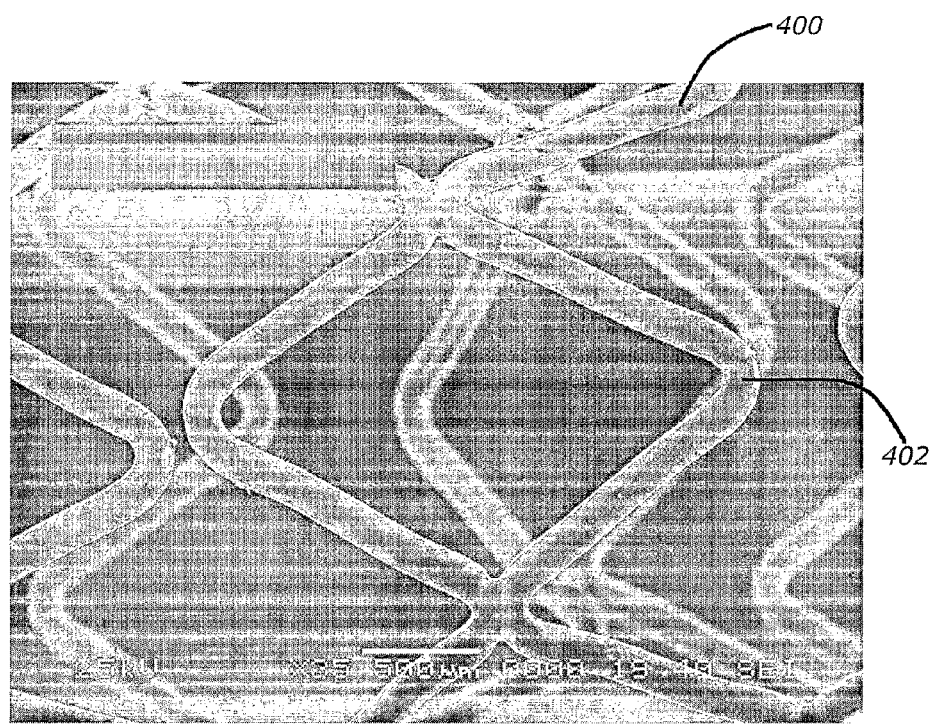
FIG. 4 depicts a vascular stent used to deliver the antirestenotic compounds of the present invention.

One embodiment of the present invention is depicted in FIG. 4. In FIG. 4 a vascular stent 400 having the structure 402 is made from a material selected from the non-limiting group of materials including stainless steel, nitinol, aluminum, chromium, titanium, ceramics, and a wide range of synthetic polymeric and natural materials including collagen, fibrin and plant fibers. The structure 402 is provided with a coating composition made in accordance with the teachings of the present invention.

Figure 5:
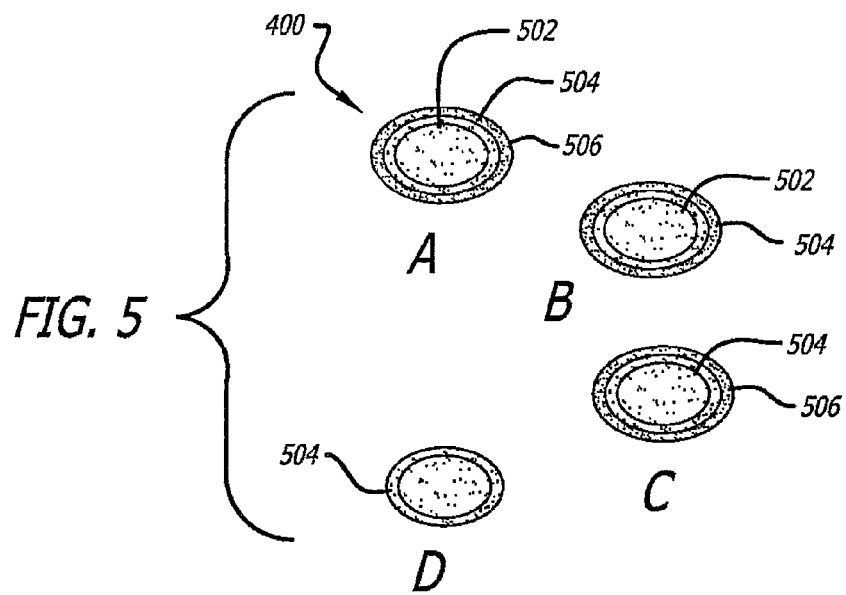
FIG. 5 depicts cross sections of medical devices (stents) having various drug-eluting coatings made in accordance with the teachings of the present invention.
Figure 6:
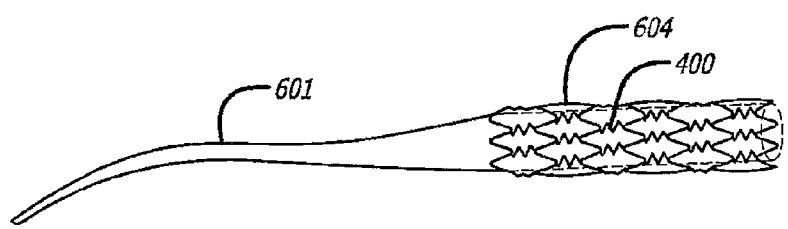
FIG. 6 depicts a balloon catheter assembly used for angioplasty and the site-specific delivery of stents to anatomical lumens at risk for restenosis.

FIG. 5a-d are cross-sections of stent 400 showing various coating configurations. In FIG. 5a stent 400 has a first polymer coating 502 comprising an optional medical grade primer, such as but not limited to parylene; a second controlled release coating 504; and a third barrier, or cap, coat 506. In FIG. 5b stent 400 has a first polymer coating 502 comprising an optional medical grade primer, such as but not limited to parylene and a second controlled release coating 504. In FIG. 5c stent 400 has a first controlled release coating 504 and a second barrier, or cap, coat 506. In FIG. 5d stent 400 has only a controlled release coating 504. FIG. 6 depicts a vascular stent 400 having a coating 604 made in accordance with the teachings of the present invention mounted on a balloon catheter 601.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The controlled-release coatings of the present invention can be applied to medical device surfaces, either primed or bare, in any manner known to those skilled in the art. Applications methods compatible with the present invention include, but are not limited to, spraying, dipping, brushing, vacuum-deposition, and others. Moreover, the controlled-release coatings of the present invention may be used with a cap coat. A cap coat as used here refers to the outermost coating layer applied over another coating. A drug-releasing copolymer coating is applied over the primer coat. A polymer cap coat is applied over the drug-releasing copolymer coating. The cap coat may optionally serve as a diffusion barrier to further control the drug release, or provide a separate drug. The cap coat may be merely a biocompatible polymer applied to the surface of the sent to protect the stent and have no effect on elution rates. One aspect of the present invention is provide a biodegradable cap coat that protects the device and bioactive agent from the environment until implanted. After implantation is complete, the biodegradable cap coat degrades at a predetermined rate (made possible by the additional and modification of functional groups to the polymer backbone as made in accordance with the teachings of the present invention) exposing the medical device surface and bioactive agent to the physiological environment.

As discussed above, medical devices can be fabricated from the polymeric compounds of the present invention using a variety of methods. For exemplary, non-limiting, purposes a biodegradable vascular stent will be described. In the one embodiment the stent is a tubular shaped member having first and second ends and a walled surface disposed between the first and second ends. The walls are composed of extruded polymer monofilaments woven into a braid-like embodiment. In the second embodiment, the stent is injection molded or extruded. Fenestrations are molded, laser cut, die cut, or machined in the wall of the tube.

In the braided stent embodiment monofilaments are fabricated from polymer materials that have been pelletized then dried. The dried polymer pellets are then extruded forming a coarse monofilament which is quenched. The extruded, quenched, crude monofilament is then drawn into a final monofilament with an average diameter from approximately 0.01 mm to 0.6 mm, preferably between approximately 0.05 mm and 0.15 mm. Approximately 10 to approximately 50 of the final monofilaments are then woven in a plaited fashion with a braid angle about 90 to 170 degrees on a braid mandrel sized appropriately for the application. The plaited stent is then removed from the braid mandrel and disposed onto an annealing mandrel having an outer diameter of equal to or less than the braid mandrel diameter and annealed at a temperature between about the polymer glass transition temperature and the melting temperature of the polymer blend for a time period between about five minutes and about 18 hours in air, an inert atmosphere or under vacuum. The stent is then allowed to cool and is then cut.

The extruded tubular stent of the present invention is formed by first melting the pelletized polymer in the barrel of an injection molding machine and then injected into a mold under pressure where it is allowed to cool and solidify. The stent is then removed from the mold. The stent made in accordance with the teachings of the present invention may, or may not, be molded with fenestrations in the stent tube. In a preferred embodiment of the fenestrated stent, the tube blank is injection molded or extruded, preferably injection molded, without fenestrations. After cooling, fenestrations are cut into the tube using die-cutting, machining or laser cutting, preferably laser cutting. The resulting fenestrations, or windows, may assume any shape which does not adversely affect the compression and self-expansion characteristics of the final stent.

The stent is then disposed on an annealing mandrel having an outer diameter of equal to or less than the inner diameter of the stent and annealed at a temperature between about the polymer glass transition temperature and the melting temperature of the polymer blend for a time period between about five minutes and 18 hours in air, an inert atmosphere or under vacuum. The stent is allowed to cool and then cut as required.

Stents made in accordance with the teachings of the present invention have mechanical properties and strength that generally increase proportionally with the molecular weight of the polymers used. The optimum molecular weight range is selected to accommodate processing effects and yield a stent with desired mechanical properties and in vivo degradation rate.

Two physical qualities of the polymer or polymer blend used to fabricate the stent play important roles in defining the overall mechanical qualities of the stent: tensile strength and tensile modulus. Tensile strength is defined as the force per unit area at the breaking point. It is the amount of force, usually expressed in pounds per square inch (psi), that a substrate can withstand before it breaks, or fractures. The tensile modulus, expressed in psi, is the force required to achieve one unit of strain which is an expression of a substrate's stiffness, or resistance to stretching, and relates directly to a stent's self-expansion properties.

Tensile strength and tensile modulus are physical properties that define a self-expanding stent's performance characteristics; these properties include compression resistance and self-expansion, or radial expansion, force. Compression resistance relates to the stent's ability to withstand the surrounding tissue's circumferential pressure. A stent with poor compression resistance will not be capable of maintaining patency. Self expansion force determines the stent's capacity to restore patency to a constricted lumen once inserted. The combination of self-expansion with resistance to compression is competing qualities and must be carefully considered when a stent is designed Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A medical device comprising a nitric oxide (NO)-releasing, biodegradable polymer according to Formula VIII:

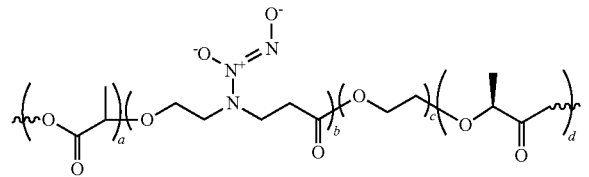

Formula VIII wherein the ratio of a:b:c:d is a=40-45, b=10-12, c=0.1-0.5 and d=40-45.

2. The medical device according to claim 1 wherein the ratio of a:b:c:d is 44:11.8:0.2:44.

3. The medical device according to any one of claim 1 wherein said medical device is selected from the group consisting of vascular stents, stent grafts, urethral stent, biliary stents, catheters, sutures, ocular devices, heart valves, shunts, pacemakers, bone screws and anchors, protective plates and prosthetic devices.

4. The medical device according to any one of claim 1 wherein said NO-releasing biodegradable polymer further comprises a bioactive agent selected from the group consisting of zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

5. A vascular stent comprising:
an NO-releasing, biocompatible, biodegradable polymer comprising ester groups, wherein at least one monomeric unit of the polymer is derived from the compound of Formula I:

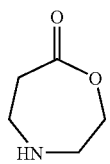

Formula 1 wherein biodegradable polymer further comprises a bioactive agent and wherein the polymer comprises a compound according to Formula VIII:

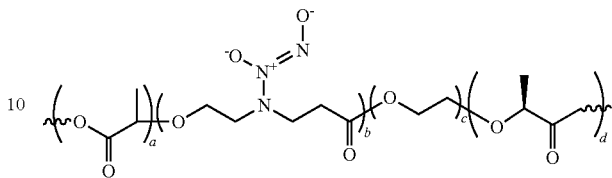

Formula VIII wherein the ratio of a:b:c:d is a=40-45, b=10-12, c=0.1-0.5 and d=40-45.

6. The vascular stent according to claim 5 wherein the ratio of a:b:c:d is 44:11.8:0.2:44.

7. A vascular stent having a NO-releasing coating comprising a biocompatible, biodegradable polymer comprising ester groups, wherein at least one monomeric unit of the polymer is derived from the compound of Formula I:

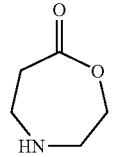

Formula 1 wherein said biodegradable polymer further comprises a zotarolimus and wherein the polymer comprises a compound according to Formula VIII:

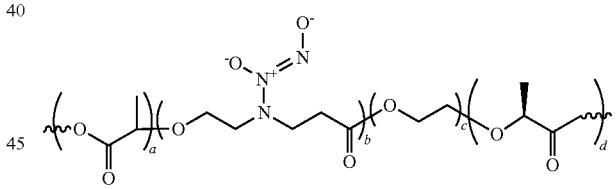

Formula VIII wherein the ratio of a:b:c:d is a=40-45, b=10-12, c=0.1-0.5 and d=40-45.

8. The vascular stent according to claim 7 wherein the ratio of a:b:c:d is 44:11.8:0.2:44.

9. A biodegradable vascular stent comprising an NO-releasing biocompatible, biodegradable polymer comprising ester groups, wherein at least one monomeric unit of the polymer is derived from the compound of Formula I:

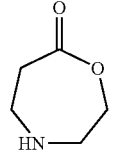

Formula 1 wherein said biodegradable polymer further comprises a zotarolimus and wherein the polymer comprises a compound according to Formula VIII:

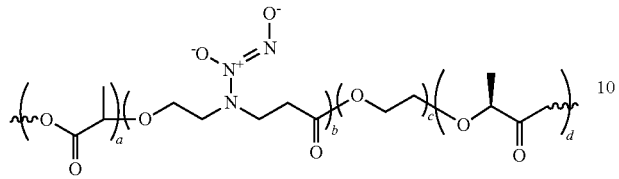

Formula VIII wherein the ratio of a:b:c:d is a=40-45, b=10-12, c=0.1-0.5 and d=40-45.

10. The vascular stent according to claim 9 wherein the ratio of a:b:c:d is 44:11.8:0.2:44.

11. An implantable medical device having a NO-releasing coating comprising a biocompatible, biodegradable polymer comprising ester groups, wherein at least one monomeric unit of the polymer is derived from the compound of Formula I:

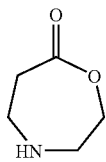

Formula 1 wherein said biodegradable polymer further comprises a zotarolimus and wherein the polymer comprises a compound according to Formula VIII:

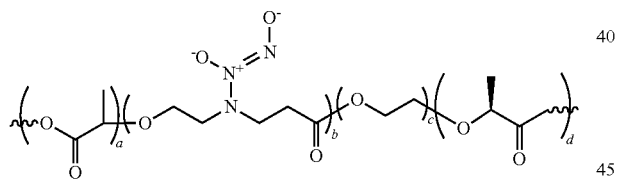

Formula VIII wherein the ratio of a:b:c:d is a=40-45, b=10-12, c=0.1-0.5 and d=40-45.

12. The vascular stent according to claim 11 wherein the ratio of a:b:c:d is 44:11.8:0.2:44.

13. A biodegradable implantable medical device comprising an NO-releasing, biocompatible biodegradable polymer comprising ester groups, wherein at least one monomeric unit of the polymer is derived from the compound of Formula I:

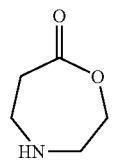

Formula 1 wherein said biodegradable polymer further comprises a zotarolimus and wherein the polymer comprises a compound according to Formula VIII:

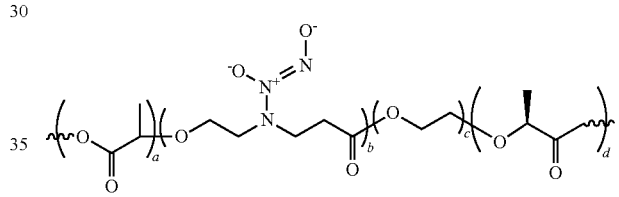

Formula VIII wherein the ratio of a:b:c:d is a=40-45, b=10-12, c=0.1-0.5 and d=40-45.

14. The vascular stent according to claim 13 wherein the ratio of a:b:c:d is 44:11.8:0.2:44.

* * * * *

UNITED STATES PATENT AND TRADEMARK OFFICE
CERTIFICATE OF CORRECTION

PATENT NO. : 8,021,679 B2
APPLICATION NO. : 12/064112
DATED : September 20, 2011
INVENTOR(S) : Mingfei Chen et al.

Page 1 of 1

It is certified that error appears in the above-identified patent and that said Letters Patent is hereby corrected as shown below:

Column 23, line 20, "(NO)-releasing, biodegradable" should be changed to --(NO)-releasing, biocompatible, biodegradable--

Column 23, line 36, "to any one of claim" should be changed to --to claim--

Column 23, line 42, "to any one of claim" should be changed to --to claim--

Signed and Sealed this
Twenty-second Day of November, 2011

David J. Kappos
*Director of the United States Patent and Trademark Office*